United States Patent
Sukhwinder et al.

(10) Patent No.: US 6,818,639 B2
(45) Date of Patent: Nov. 16, 2004

(54) PHARMACEUTICAL COMBINATION FORMULATION AND METHOD OF TREATMENT WITH THE COMBINATION

(75) Inventors: Jossan Sukhwinder, Uppsala (SE); Björn M. Nilsson, Uppsala (SE); Kjell S. Sakariassen, Hässelby (SE); Jan Svartengren, Uppsala (SE)

(73) Assignee: Biovitrum AB, Stockholm (SE)

( * ) Notice: Subject to any disclaimer, the term of this patent is extended or adjusted under 35 U.S.C. 154(b) by 56 days.

(21) Appl. No.: 09/908,801

(22) Filed: Jul. 20, 2001

(65) Prior Publication Data

US 2002/0068732 A1 Jun. 6, 2002

Related U.S. Application Data

(60) Provisional application No. 60/222,283, filed on Aug. 1, 2000.

(30) Foreign Application Priority Data

Jul. 21, 2000 (SE) .............................................. 0002754

(51) Int. Cl.⁷ .......................... A61K 31/55; A61K 31/50
(52) U.S. Cl. .............................. 514/217.01; 514/252.13
(58) Field of Search ........................ 514/252.13, 217.01

(56) References Cited

FOREIGN PATENT DOCUMENTS

| WO | WO 98/27081 | 6/1998 |
| WO | WO 99/65906 | 12/1999 |
| WO | WO 00/12510 | 3/2000 |

OTHER PUBLICATIONS

Dourish, "Multiple Serotonin Receptors: Opportunities for New Treatments for Obesity?," Obesity Research, 3(Supp. 4):449S–462S, Nov. 1995.
Kordik et al., "Pharmacological Treatment of Obesity: Therapeutic Strategies," Journal of Medicinal Chemistry, 42(2):181–201, Jan. 28, 1999.

*Primary Examiner*—Zohreh Fay
(74) *Attorney, Agent, or Firm*—Fish & Richardson P.C.

(57) ABSTRACT

The invention relates to method of preventing or treating a disease related to the $5\text{-HT}_{2C}$ receptor and the $5\text{-HT}_6$ receptor, comprising administering to a human or animal subject in need thereof a $5\text{-HT}_{2C}$ receptor agonist and a $5\text{-HT}_6$ receptor antagonist in sufficient amounts to provide a therapeutic effect. The invention also relates to a pharmaceutical composition comprising an effective amount of a combination of a $5\text{-HT}_{2C}$ receptor agonist and a $5\text{-HT}_6$ receptor antagonist, and optionally a pharmaceutically acceptable carrier.

19 Claims, 2 Drawing Sheets

PHARMACEUTICAL COMBINATION FORMULATION AND METHOD OF TREATMENT WITH THE COMBINATION

This application claims the benefit of provisional application 60/222,283 filed Aug. 1, 2000.

TECHNICAL FIELD

The present invention relates to the prophylaxis or treatment of a 5-$HT_{2C}$ and a 5-$HT_6$ receptor-related disease. In addition, the invention provides a pharmaceutical composition containing a 5-$HT_{2C}$ receptor agonist and a 5-$HT_6$ receptor antagonist for therapeutic use.

BACKGROUND ART

Serotonin (5-hydroxytryptamine or 5-HT) is a key neurotransmitter of the peripheral and central nervous system (PNS and CNS) and has been implicated in a variety of sensory, motor and behavioral functions such as regulation of eating, sleeping, body temperature, blood pressure, emotions and cognition. At least 14 distinct serotonin receptor subtypes are expressed in the mammalian PNS and CNS and have been formally classified; see Glennon, et al., *Neurosci. Biobehav. Rev.* 1990, 14, 35–37; and D. Hoyer, et al., *Pharmacol. Rev.* 1994, 46, 157–203. Serotoninergic agonists and antagonists have been suggested for the treatment of a wide range of disorders, including anxiety, depression, hypertension, migraine, obesity, drug abuse and addiction, compulsive disorders, schizophrenia, autism, neurodegenerative disorders (e.g. Alzheimer's disease, Parkinsonism, and Huntington's chorea), and chemotherapy-induced vomiting.

The 5-$HT_2$ subfamily of receptors is composed of three subtypes, the 5-$HT_{2A}$, 5-$HT_{2B}$ and 5-$HT_{2C}$ receptors. Serotonin 5-$HT_{2C}$ receptors are expressed in many brain regions and have been implicated in the regulation of food intake (Dourish, C. T. *Obes. Res.* 1995, 3, Suppl. 4, 449S-462S; Bickerdike, M. J., et al. *Diabetes, Obes. Metab.* 1999, 1, 207–214). It has been demonstrated that the non-specific 5-$HT_{2C}$ receptor agonist m-chlorophenylpiperazine (m-CPP), which has some preference for the 5-$HT_{2C}$ receptor, reduces food intake in mice that express the normal 5-$HT_{2C}$ receptor while the compound lacks activity in mice expressing the mutated inactive form of the 5-$HT_{2C}$ receptor (Tecott, L. H., et al. *Nature* 1995, 374, 542–546).

Moreover, it has been reported that m-CPP and the azepinoindole U-22394A, the latter recently identified to be a 5-$HT_{2C}$ receptor agonist (unpublished observation), reduce body weight in humans following two and nine weeks of treatment, respectively (Walsh, A. E. S., *Psychopharmacology* 1994, 116, 120–122; Sargent, P. A., et al. *Psychopharmacology* 1997, 133, 309–312 and Gallant, D. M., et al. *Curr. Ther. Res.* 1967, 9, 579–581).

Recently, a series of pyrrolo[3,2,1-ij]quinoline derivatives was identified to be 5-$HT_{2C}$ receptor agonists having selectivity over the 5-$HT_{2A}$ receptor (Isaac M., et al., *Bioorg. Med. Chem. Lett.* 2000, 10, 919–921). The compounds are said to offer a novel approach to the treatment of obesity and epilepsy.

The 5-$HT_{2C}$ receptor subtype has also been suggested to be involved in CNS disorders, such as depression and anxiety (Jenck, F., et al. *Expert Opin. Invest. Drugs* 1998, 7,1587–1599; Leysen, D. C. M. *IDrugs* 1999, 2, 109–120). The 5-$HT_{2C}$ receptor subtype has further been suggested to be involved in urinary disorders such as urinary incontinence (Leysen, D. C. M. *IDrugs* 1999, 2, 109–120).

Also the 5-$HT_6$ receptor (identified in 1993-Monsma et al., *Mol. Pharmacol.* 1993, 43, 320–327 and Ruat, M. et al. *Biochem. Biophys. Res. Commun.* 1993, 193, 269–276) has been implicated in the regulation of food intake and CNS disorders.

Thus, for example, Bentley, J. C., et al., *Br. J. Pharmacol.* 1999, 126, 66P describes food intake reduction in rats by the administration of a 5-$HT_6$ antagonist. Also, several antidepressants and atypical antipsychotics display high affinity for the 5-$HT_6$ receptor which have suggested the involvement of the 5-$HT_6$ receptor in schizophrenia (Roth et al. *J. Pharmacol. Exp. Ther.* 1994, 268, 1403–1410; Sleight et al. *Expert Opin. Ther. Patents* 1998, 8, 1217–1224; Bourson et al. *Br. J. Pharm.* 1998, 125, 1562–1566; Boess et al. *Mol. Pharmacol.* 1998, 54, 577–583; Sleight et al. *Br. J. Pharmacol.* 1998, 124, 556–562). In addition, the 5-$HT_6$ receptor has been linked to generalized stress and anxiety states (Yoshioka et al. *Life Sci.* 1998, 17/18, 1473–1477).

SUMMARY OF THE INVENTION

According to the present invention it has now unexpectedly been found that the combined administration of a 5-$HT_{2C}$ receptor agonist and a 5-$HT_6$ receptor antagonist reduces food intake by more than the administration of either agonist or antagonist alone. Such combined administration of a 5-$HT_{2C}$ receptor agonist and a 5-$HT_6$ receptor antagonist may offer therapeutic advantages as compared to treatment with either agonist or antagonist alone.

One aspect of the present invention therefore provides a pharmaceutical composition comprising an effective amount of a combination of a 5-$HT_{2C}$ receptor agonist and a 5-$HT_6$ receptor antagonist, and optionally a pharmaceutically acceptable carrier.

Another aspect of the invention provides a method of preventing or treating a disease, in particular obesity, related to the 5-$HT_{2C}$ receptor and the 5-HT6 receptor, comprising administering to a human or animal subject in need thereof a 5-$HT_{2C}$ receptor agonist and a 5-$HT_6$ receptor antagonist (simultaneously or sequentially) in sufficient amounts to provide a therapeutic effect.

Still another aspect of the invention provides the use of a 5-$HT_{2C}$ receptor agonist and a 5-$HT_6$ receptor antagonist for the manufacture of a medicament for the treatment of a disease related to the 5-$HT_{2C}$ receptor and the 5-$HT_6$ receptor.

Another aspect of the invention provides a process for preparing a pharmaceutical composition, wherein a 5-$HT_{2C}$ receptor agonist and a 5-$HT_6$ receptor antagonist in a combined therapeutic amount are intimately mixed with a pharmaceutically acceptable carrier.

Yet another aspect of the invention provides a product containing a 5-$HT_{2C}$ receptor agonist and a 5-$HT_6$ receptor antagonist as a combined preparation for simultaneous, separate or sequential use in therapy of a disease, in particular obesity, related to the 5-$HT_{2C}$ receptor and the 5-$HT_6$ receptor.

DETAILED DESCRIPTION OF THE INVENTION

Figure 1:
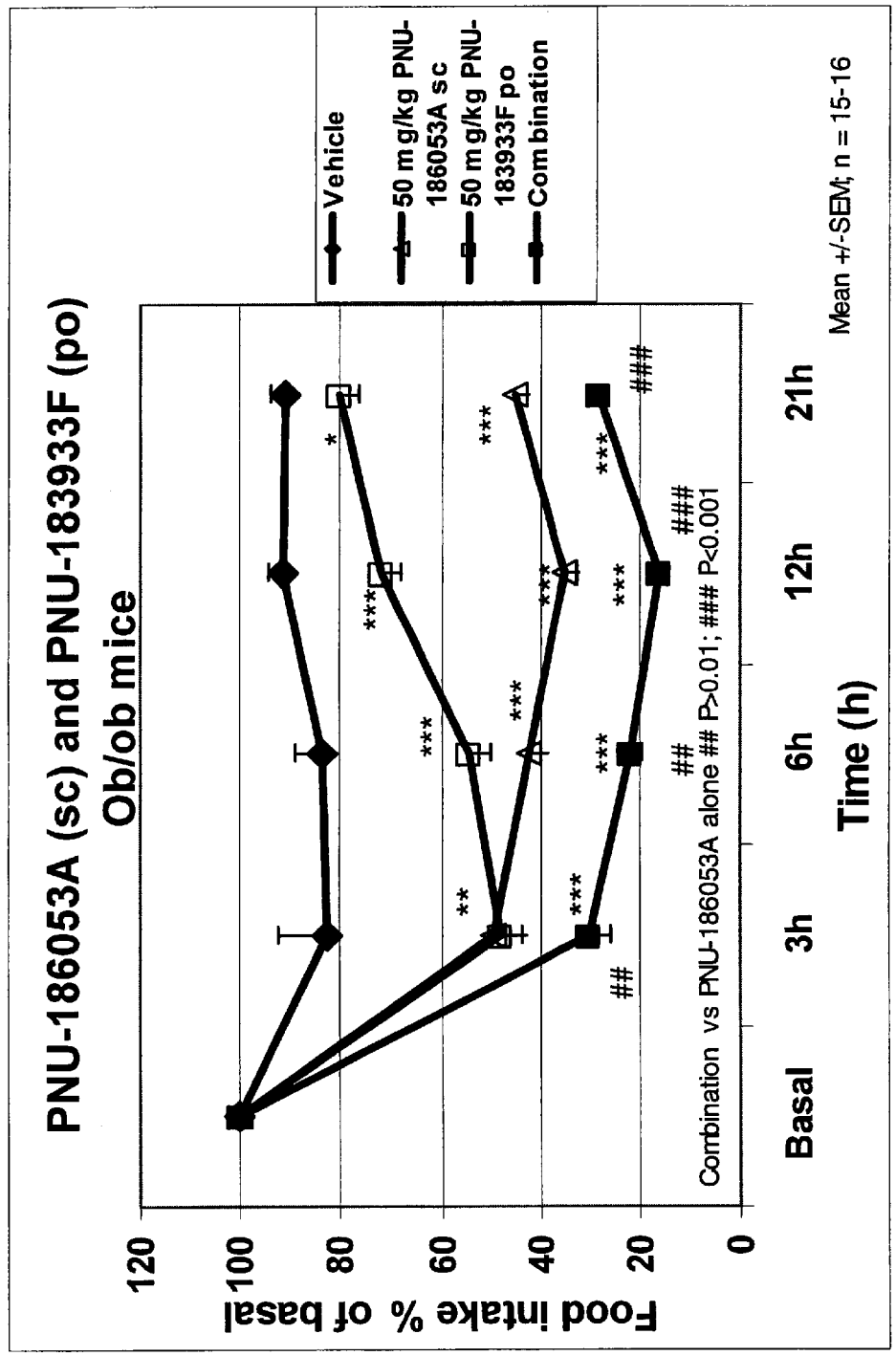
FIG. 1 shows the effect on food intake in ob/ob mice following combined administration with a 5-$HT_{2C}$ receptor agonist (PNU-183933F; 50 mg/kg po) and a 5-$HT_6$ receptor antagonist (PNU-186053A; 50 mg/kg sc), as well as the effect of each agonist and antagonist alone.

As mentioned above, the present invention is based on the unexpected finding that combined administration of a 5-HT$_{2C}$ receptor agonist and a 5-HT$_6$ receptor antagonist reduces food intake more than either agonist or antagonist alone. Such combined administration of a 5-HT$_{2C}$ receptor agonist and a 5-HT$_6$ receptor antagonist may also offer several benefits, for instance in the treatment of obesity, as compared to treatment with either agonist or antagonist alone.

Firstly, the combined administration requires lower doses of each compound to yield similar or improved reduction of food intake than mono-therapy.

Secondly, the lower doses required by the combined administration may reduce the risk of adverse events.

Thirdly, the lower doses required by the combined administration may reduce the risk of tolerance development and abuse liability.

Fourthly, therapy based on two targets may increase the individual therapeutic efficacy relative to therapy based on one target. The risk of non-responsive efficacy (non-responders) may be reduced as well.

The beneficial effects of the combined administration of this invention is useful not only for the modulation of eating behavior, and for treating over-weight and obesity, but may also be useful for the treatment of CNS disorders such as, depression, mania, schizophreniform disorders, anxiety, memory disorders (such as Alzheimer's disease) migraine headache, drug addiction, convulsive disorders, personality disorders, post-traumatic stress syndrome, and sleep disorders as well as for treatment of urinary incontinence (or more generally overactive bladder), sexual dysfunctions, gastrointestinal disorders and glaucoma.

The term "5-HT$_{2C}$ receptor agonist" as used herein refers to a compound that causes activation of the serotonin 5-HT$_{2C}$ receptor. The 5-HT$_{2C}$ receptor agonist preferably has an affinity constant, K$_i$, of less than 50 nM, preferably less than 20 nM, and an in vitro intrinsic activity, measured as intracellular Ca$^{2+}$ levels, greater than 20%, preferably greater than 50%, relative to 5-HT (1 $\mu$M).

The term "5-HT$_6$ receptor antagonist" as used herein refers to a compound that causes blockade of the serotonin 5-HT$_6$ receptor mediated responses. The 5-HT$_6$ receptor antagonist preferably has an affinity constant, K$_i$, of less than 50 nM, preferably less than 20 nM, and an in vitro intrinsic activity, measured as intracellular cAMP levels, less than 50%, preferably less than 20%, relative to 5-HT (1 $\mu$M).

In vitro assays that may be used for determining the affinity and the intrinsic activity, respectively, of 5-HT$_{2C}$ receptor agonists and 5-HT$_6$ receptor antagonists are known in the art and are also given in the Experimental Part below, as are assays for determining affinity to 5-HT$_{2A}$ and 5-HT$_{2B}$ receptors.

Generally, the 5-HT$_{2C}$ receptor agonists and 5-HT$_6$ receptor antagonists should be sufficiently selective not to cause any substantial adverse side effects. The terms "selective" and "substantial" in this context are, however, to be interpreted broadly, the meanings thereof being readily apparent to the skilled person.

The 5-HT$_{2C}$ receptor agonist preferably has a selectivity for the 5-HT$_{2C}$ receptor of at least 5, preferably at least 10 and more preferably at least 20, relative to the 5-HT$_{2A}$, 5-HT$_{2B}$ and 5-HT$_6$ receptors, respectively (measured as the affinity ratios 5-HT$_{2A}$/5-HT$_{2C}$, 5-HT$_{2B}$/5-HT$_{2C}$ and 5-HT$_6$/5-HT$_{2C}$).

The 5-HT$_6$ receptor antagonist preferably has a selectivity for the 5-HT$_6$ receptor of at least 5, preferably at least 10 and more preferably at least 20, relative to the 5-HT$_{2A}$, 5-HT$_{2B}$ and 5-HT$_{2C}$ receptors, respectively (measured as the affinity ratios 5-HT$_{2A}$/5-HT$_6$, 5-HT$_{2B}$/5-HT$_6$ and 5-HT$_{2C}$/5-HT$_6$).

Relevant tests to determine whether a compound is a selective 5-HT$_{2C}$ receptor agonist or a selective 5-HT$_6$ receptor antagonist are known in the art, and are, as mentioned above, also outlined in the Experimental Part below.

Compounds known to be 5-HT$_{2C}$ receptor agonists are, for example, azetidine and pyrrolidine derivatives of the type described in EP-A-0863136; tricyclic pyrrole derivatives of the type described in EP-A-0657426; 1-aminoethylindoles of the type described in EP-A-0655440; pyrazinoindoles of the type described in EP-A-0572863; piperazinylpyrazines of the type described in U.S. Pat. No. 4,081,542; indoline derivatives of the type described in WO 00/12475; pyrroloindoles, pyridoindoles and azepinoindoles of the type described in WO 00/12510; indazole derivatives of the type described in WO 00/12482; pyrroloquinolines of the type described in WO 00/12502; 2,3,4,4a-tetrahydro-1H-pyrazino[1,2-a]quinoxalin-5(6H) ones of the type described in WO 00/35922; indazolylpropylamines of the type described in WO 00/12481; indazoles of the type described in WO 00/17170; piperazinylpyrazines of the type described in WO 00/76984 and in Swedish patent applications Nos. 0004244-0 and 0004245-7, filed on Nov. 20, 2000; heterocycle fused $\gamma$-carbolines of the type described in WO 00/77001, WO 00/77002 and WO 00/77010; benzofurylpiperazines of the type described in WO 01/09111 and WO 01/09123; benzofurans of the type described in WO 01/09122; benzothiophenes of the type described in 01/09126; pyridinylpiperazines of the type described in EP 370560; pyrroloquinolines of the type described in Bioorg. Med. Chem. Lett. 2000, 10, 919–921; aminoalkylindazoles of the type described in WO 98/30548; indoles of the type described in WO 01/12603; indolines of the type described in WO 01/12602; pyrazino(aza)indoles of the type described in WO 00/44753; tricyclic pyrroles or pyrazoles of the type described in WO 98/56768.

Currently preferable 5-HT$_{2C}$ receptor agonists are of the arylpiperazine and piperazinylpyrazine compound classes, in particular compounds disclosed in WO 00/76984 and in Swedish patent applications Nos. 0004244-0 and 0004245-7, filed on Nov. 20, 2000.

Compounds known to be 5-HT$_6$ receptor antagonists are, for example, piperazinylbenzenesulfonamides of the type described in WO 99/37623; sulfonylbenzene derivatives of the type described in EP-A-0930302; sulfonamide derivatives of the type described in WO 99/02502; sulfonamide derivatives of the type described in WO 99/42465; sulfonamide derivatives of the type described in WO 98/27081; carboxamide derivatives of the type described in WO 98/27058; sulfonamide derivatives of the type described in EP-A-0815861; pyrrolidonomethylindole derivatives of the type described in WO 99/47516; bicyclic piperidine and piperazine derivatives of the type described in WO 99/65906; pyrazolopyrimidine and pyrazolotriazine derivatives of the type described in EP-A-0941994; arylsulfone-substituted hexahydroazepinoindoles of the type described in WO 01/05793; oxazinocarbazoles of the type described in WO 01/09142; aminoalkoxycarbazoles of the type described in WO 01/17963; diphenylsulfones of the type described in the international patent application PCT/US00/30177, filed on Jun. 20, 2000; and arylsulfonylindoles of the type described in the Swedish patent application No. 0003810-9, filed on Oct. 20, 2000.

Currently preferable 5-HT$_6$ receptor antagonists include the azepinoindole compound class, such as the class of arylsulfone-substituted hexahydroazepinoindoles compounds disclosed in WO 01/05793. Other preferred 5-HT$_6$ receptor antagonists include the arylsulfonylindole compound class, such as the compound class described in the Swedish patent application No. 0003810-9.

The 5-HT$_{2C}$ receptor agonists and the 5-HT$_6$ receptor antagonists may be the compounds as such or where appropriate the pharmaceutically acceptable salts (acid or base addition salts) thereof or stereochemically isomeric forms thereof (including optical isomers, such as enantiomers and racemates).

The pharmaceutically acceptable addition salts as mentioned above are meant to comprise the therapeutically active non-toxic acid and base addition salt forms which the compounds are able to form. Compounds which have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as acetic acid, propanoic acid, hydroxyacetic acid, lactic acid, pyruvic acid, glycolic acid, maleic acid, malonic acid, oxalic acid, benzenesulfonic acid, toluenesulfonic acid, methanesulfonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The 5-HT$_{2C}$ receptor agonists and the 5-HT$_6$ receptor antagonists may also be prodrugs or forms that may release the active ingredient in question after metabolic tranformation in vivo. Conventional procedures for the selection and preparation of suitable prodrug derivatives are described, for example, in "Design of Prodrugs" ed. H. Bundgaard, Elsevier, 1985.

The 5-HT$_{2C}$ receptor agonists and the 5-HT$_6$ receptor antagonists may be formulated into various pharmaceutical forms for administrative purposes, either in the same pharmaceutical dosage form, such as in the same tablet, or in separate pharmaceutical dosage forms. In the latter case, however, it may be advantageous to put the 5-HT$_{2C}$ receptor agonist unit dosage form and the 5-HT$_6$ receptor antagonist unit dosage form in the same package, for example in the same blister.

The 5-HT$_{2C}$ receptor agonists and the 5-HT$_6$ receptor antagonists, in the form of free bases or salt, can be brought into suitable galenic forms, such as compositions for oral use, for injection, for nasal spray administration or the like, in accordance with accepted pharmaceutical procedures. Such pharmaceutical compositions according to the invention comprise an effective amount of a 5-HT$_{2C}$ receptor agonist and a 5-HT$_6$ receptor antagonist in association with compatible pharmaceutically acceptable carrier materials, or diluents, as are well known in the art. The carriers may be any inert material, organic or inorganic, suitable for oral, enteral, rectal, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavoring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

The dose level of each of the specific 5-HT$_{2C}$ receptor agonist and 5-HT$_6$ receptor antagonist, and the frequency of dosage of the specific combination will vary depending on a variety of factors including the potency of each specific compound employed, the metabolic stability and length of action of that compound, the patient's age, body weight, general health, sex, diet, mode and time of administration, rate of excretion, drug combination, the severity of the condition to be treated). The daily dosage may, for example, range from about 0.001 mg to about 150 mg per kilo of body weight, preferably from about 0.01 mg to about 100 mg per kilo of body weight, especially from about 0.1 to about 50 mg per kilo of body weight of each of the 5-HT$_{2C}$ receptor agonist and of the 5-HT$_6$ receptor antagonist, administered singly or multiply in doses, e.g. dosages of from about 0.01 mg to about 1 g each. Usually, such a combined dosage is given orally but e.g. parenteral or rectal administration may also be chosen. An exemplary tablet combination formulation may be in the form of either (A) two separate tablets, i.e. one tablet containing 10 mg, 20 mg or 50 mg of a 5-HT$_{2C}$ receptor agonist, and one tablet containing 10 mg, 20 mg or 50 mg of a 5-HT$_6$ receptor antagonist; or (B) a combined tablet containing 10 mg, 20 mg or 50 mg of a 5-HT$_{2C}$ receptor agonist and 10 mg, 20 mg or 50 mg of a 5-HT$_6$ receptor antagonist.

The invention will now be illustrated further by the following non-limiting Experimental Section.

EXPERIMENTAL SECTION

A. Preparation of Test Compounds

The free base of the 5-HT$_{2C}$ receptor agonist (2R)-methyl-1-{3-[2-(3-pyridinyloxy)ethoxy]-2-pyrazinyl}piperazine, fumarate ("PNU-183933F") was prepared as described in WO 00/76984. The free base was converted to its fumarate salt, m.p. 126–129° C. MS m/z 315 (M)$^+$. Anal. (C$_{16}$H$_{21}$N$_5$O$_2$.C$_4$H$_4$O$_4$) C, H, N.

The 5-HT$_6$ receptor antagonist 6-methyl-9-(phenylsulfonyl)-1,2,3,4,5,6-hexahydroazepino[4,5-b]indole, hydrochloride ("PNU-186053A") was prepared as described in WO 01/05793.

The 5-HT$_{2C}$ receptor agonist (2R)-1-(3-{2-[(2-ethoxy-3-pyridinyl)oxy]ethoxy}-2-pyrazinyl)-2-methylpiperazine, fumarate ("BVT.2938F") was prepared as described in WO 00/76984.

The 5-HT$_6$ receptor antagonist 1-(phenylsulfonyl)-4-(1-piperazinyl)-1H-indole, hydrochloride ("BVT.5182C") was prepared as described in Swedish patent application No. 0003810-9, filed on Oct. 20, 2000. Briefly, BVT.5182C was prepared according the general procedure depicted in Scheme 1, below, starting from commercially available 4-piperazinoindole (compound 1) that undergoes steps (a) to (c) to afford 1-(phenylsulfonyl)-4-(1-piperazinyl)-1H-indole, hydrochloride (yield 80%). HPLC purity >95%; $^1$H NMR (DMSO-d6) δ9.64 (br s, 2 H), 8.00–7.85 (m, 3 H), 7.79 (d, J=3.77 Hz, 1 H), 7.70–7.65 (m, 1 H), 7.63–7.60 (m, 3 H), 7.27–7.22 (m, 1 H), 6.95 (d, J=3.76 Hz, 1 H), 6.81–6.77 (m, 1 H), 3.30–3.20 (m, 4 H); $^{13}$C NMR (DMSO-d6) δ144.79, 137.02, 135.22, 134.62, 129.82, 126.85, 125.63, 125.54, 123.49, 111.15, 107.87, 107.76, 47.81, 42.86; MS (posES-FIA) m/z 342 (M+H).

Scheme 1

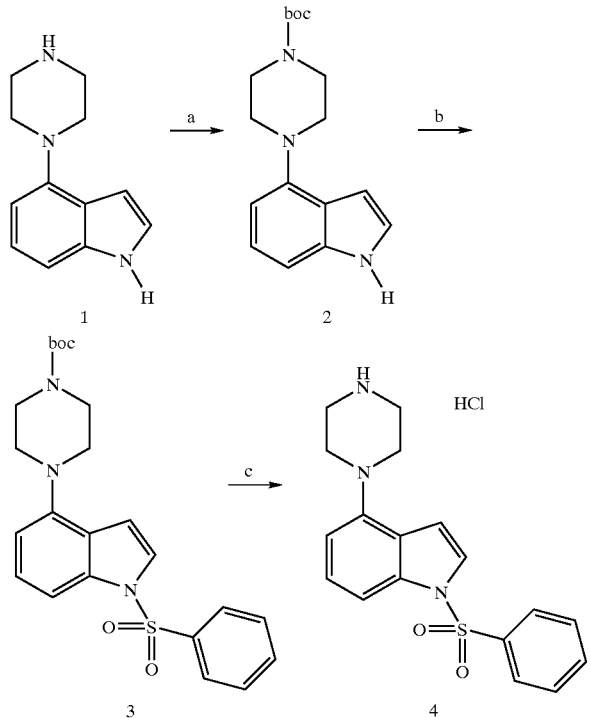

Step (a): BOC Protection of the Piperazine N4 Nitrogen

4-Piperazinoindole (1 eq), DMAP (0.1 eq) and Et$_3$N (4 eq) were dissolved in DMF. (BOC)$_2$O (1.1 eq) was added and the reaction mixture was stirred at room temperature (12 h). DMF was evaporated and the residue was purified by chromatography on silica gel using a mixture of chloroform, methanol and ammonia as eluent. HPLC: 100% purity. MS m/z 302.2 (M+H).

Step (b): Preparation of Intermediate 3

The intermediate 2 (1.0 eq) was dissolved in DMF and NaH (1.3 eq) was added and the suspension was stirred for 0.5 h under nitrogen atmosphere. Benzenesulfonyl chloride (1.2 eq) was added and the reaction was stirred overnight at room temperature. The volatiles were evaporated. The residue was dissolved in DCM, washed with a saturated solution of NaHCO$_3$, dried (MgSO$_4$), filtered and concentrated to give an oily residue that was purified by chromatography on silica gel using a mixture of hexane and ethylacetate (7:3) as eluent to give tert butyl 4-[1-(benzenesulfonyl)-1H-indol-4-yl)]-1-piperazinecarboxylate (3). HPLC 100%. NMR ($^1$H and $^{13}$C) and MS analyses support the stated structure.

Step (c): Removal of the BOC protecting group

The BOC group on intermediate 3 was removed by dissolving the compound in methanol followed by addition of ether saturated with HCl gas. The HCl salt (4) was filtered and dried.

B. Preparation of a Pharmaceutical Composition

| Tablet | | |
|---|---|---|
| | Ingredients | mg/tablet |
| 1. | 5-HT$_{2C}$ receptor agonist | 10.0 |
| 2. | 5-HT$_6$ receptor antagonist | 10.0 |
| 3. | Cellulose, microcrystalline | 57.0 |
| 4. | Calcium hydrogen phosphate | 15.0 |
| 5. | Sodium starch glycolate | 5.0 |
| 6. | Silicon dioxide, colloidal | 0.25 |
| 7. | Magnesium stearate | 0.75 |

The active ingredients 1 and 2 are mixed with ingredients 3, 4, 5 and 6 for about 10 minutes. The magnesium stearate (7) is then added, and the resultant mixture is mixed for about 5 minutes and compressed into tablet form with or without film-coating.

C. Receptor Affinity and Efficacy Assays

5-HT$_{2C}$ Receptor Affinity Assay

5-HT$_{2C}$ receptor affinity is determined in competition experiments, where the ability of a compound in serial dilution to displace $^3$H-labeled 5-HT, bound to membranes prepared from a transfected HEK293 cell line stably expressing the human 5-HT$_{2C}$ receptor protein, is monitored by Scintillation Proximity Assay (SPA) technology. Non-specific binding is defined using 5 µM mianserin.

5-HT$_{2A}$ Receptor Affinity Assay

5-HT$_{2A}$ receptor affinity is determined in competition experiments, where the ability of a compound in serial dilution to displace $^3$H-labeled ketanserin or lysergic acid diethylamide (LSD), bound to membranes prepared from a transfected CHO cell line stably expressing the human 5-HT$_{2A}$ receptor protein, is monitored by measuring the radioactivity of filtered membrane homogenates on glass fiber filters in a scintillation counter. Non-specific binding is defined using 5 µM mianserin.

5-HT$_{2B}$ Receptor Affinity Assay

5-HT$_{2B}$ receptor affinity is determined in competition experiments, where the ability of a compound in serial dilution to displace $^3$H-labeled 5-HT, bound to membranes prepared from a transfected CHO cell line stably expressing the human 5-HT$_{2B}$ receptor protein, is monitored by Scintillation Proximity Assay (SPA) technology. Non-specific binding is defined using 5 µM mianserin.

5-HT$_{2C}$ Receptor Efficacy Assay

The agonist efficacy at the 5-HT$_{2C}$ receptor is determined by the ability of a compound to mobilise intracellular calcium in transfected HEK293 cells, stably expressing the human 5-HT$_{2C}$ receptor protein, using the calcium-chelating fluorescent dye FLUO-3 (Sigma, St. Louis, Mo., U.S.A.). Relative efficacy (%) is measured relative to that of serotonin at 1 µM.

5-HT$_6$ Receptor Affinity Assay

The radioligand binding assay uses [$^3$H]-lysergic acid diethylamide (LSD). The assay is carried out in 96-well sample plates by the addition of 11 µl of the test compound at the appropriate dilution (the assay employs 11 serial concentrations of samples run in duplicate), 11 µl of radioligand, and 178 µl of a washed mixture of WGA-coated SPA beads and membranes in binding buffer prepared from HEK293-cells containing cloned human 5-HT$_6$ receptor. The plates are shaken for about 5 minutes and then incubated at room temperature for 1 hour. The plates are then loaded into counting cassettes and counted in a scintillation counter. The specifically bound cpm obtained are fit to a one-site binding model using GraphPad Prism ver. 2.0. Estimated $IC_{50}$ values are converted to $K_i$ (affinity constant) values using the Cheng-Prusoff equation (Cheng, Y. C. et al., *Biochem. Pharmacol.* 1973, 22, 3099–3108).

$5\text{-}HT_6$ Receptor Efficacy Assay

The antagonist potency at the $5\text{-}HT_6$ receptor is determined by the ability of a compound to antagonize the increase in cAMP induced by 5-HT in HEK293 cells, stably expressing the human $5\text{-}HT_6$ receptor protein, using a cAMP SPA direct screening assay system (RPA559, Amersham Pharmacia Biotech, Uppsala, Sweden).

D. Food Intake Test

Test Compounds $5\text{-}HT_{2C}$ receptor agonists (2R)-methyl-1-{3-[2-(3-pyridinyloxy)ethoxy]-2-pyrazinyl}piperazine, fumarate ("PNU-183933F") and (2R)-1-(3-{2-[(2-ethoxy-3-pyridinyl)oxy]ethoxy}-2-pyrazinyl)-2-methylpiperazine, fumarate ("BVT.2938F") were dissolved in saline (0.9% NaCl) and diluted in the same vehicle to the appropriate concentration.

$5\text{-}HT_6$ receptor antagonists 6-methyl-9-(phenylsulfonyl)-1,2,3,4,5,6-hexahydroazepino[4,5-b]indole, hydrochloride ("PNU-186053A") and 1-(phenylsulfonyl)-4-(1-piperazinyl)-1H-indole, hydrochloride (5-$HT_6$ receptor antagonist ("BVT.5182C") were dissolved and diluted in 25% cyclodextrin.

Fresh solutions were prepared on the day of treatment.

Animals

Male mice 8–9 weeks old (C57BL/6JBom-Lep$^{ob}$ (ob/ob), Bomholtsgaard, Denmark) with an average body weight of 45 g were used. The animals were housed singly in cages at 23±1° C., 40–60% humidity and had free access to water and standard laboratory chow. The 12/12 h light/dark cycle was set to lights off at 5 p.m. The animals were conditioned for at least one week before start of study. During experimental sessions, the animals obtained special chow (BioServ, Frenchtown, N.J., USA dust-free precision pellets weighing 20 mg each).

Experimental Section

At the start of the study the animals were transferred to special cages "operant test cages" (Habitest Modular Animal Behavior Test System; Colbourn Instr, Allentown, Pa., USA). These cages consist of a feeder trough with sensors for measurement of food intake, an optic lickometer for registration of water intake and an infrared-based monitor for recording overall general motor activity. The monitors are coupled to a computer, which controls and monitor events continuously. Food pellets were weighed to the amount needed for one whole study and water bottles were filled with fresh tap water and weighed. The animals were conditioned to their new environment for three days to establish baseline values. The animals were weighed at 3 p.m. at the start and at the end of the study. The compounds were administered between 4.20 and 5.00 p.m. before dark onset. Three groups of animals received (i) 5-$HT_6$ antagonist in 25% cyclodextrin; (ii) 5-$HT_{2C}$ agonist in saline; and (iii) the combination 5-$HT_{2C}$ agonist/5-$HT_6$ antagonist, respectively. When combined, 5-$HT_6$ antagonist or saline was administered 30 min before administration of the 5-$HT_{2C}$ agonist or 25% cyclodextrin. A fourth group received respectively vehicle administered in the same way. The study ended on the fifth day. Weighing was performed with a computer-assisted Mettler-Toledo PR5002/PR802 balance.

Evaluation of Results

Each dose group consisted of 12–16 animals. Data were corrected for food spillage based on the weighed spillage during 22 hours and assumed to be proportional over time. Calculations were performed for the data before and after treatment. The values were expressed as % of basal food intake (mean±SEM) for the difference between food intake before treatment and 3 h (5 pm–8 pm), 6 h (5 pm–11 pm), 12 h (5 pm–5 am), 21 h (5 pm–2 pm).

Figure 2:
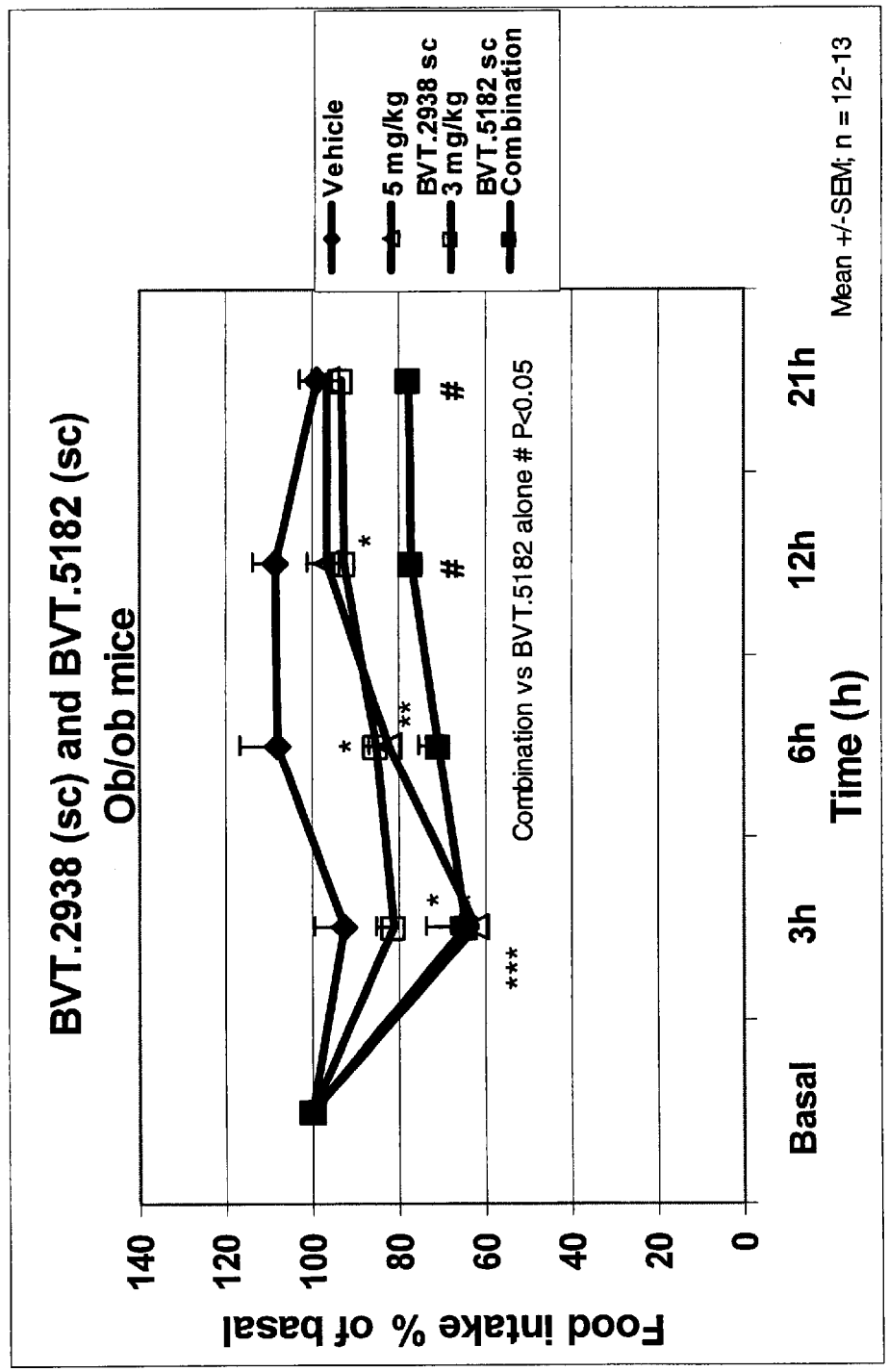
FIG. 2 shows the effect on food intake in ob/ob mice following combined administration of a 5-$HT_{2C}$ receptor agonist (BVT.2938F; 5 mg/kg sc) and a 5-HT$_6$ receptor antagonist (BVT.5182C; 3 mg/kg sc), as well as the effect of each agonist and antagonist alone.

The results shown in FIG. 1 indicate that combined treatment with the 5-$HT_6$ receptor antagonist "PNU-186053A" (50 mg/kg subcutaneously) and the 5-$HT_{2C}$ receptor agonist "PNU-183933F" (50 mg/kg per orally) decreased food consumption significantly more than the compounds given alone. Correspondingly, the results shown in FIG. 2 indicate that combined treatment with the 5-$HT_{2C}$ receptor agonist "BVT.2938F" (5 mg/kg subcutaneously) and the 5-$HT_6$ receptor antagonist "BVT.5182C" (3 mg/kg subcutaneously) decreased food consumption, at 12 and 21 hours following administration, significantly more than the compounds given alone. Thus, it is apparent that combined therapy with a 5-$HT_{2C}$ receptor agonist and a 5-$HT_6$ receptor antagonist reduces food intake more efficiently as compared to treatment with either agonist or antagonist alone.

What is claimed is:

1. A pharmaceutical composition comprising an effective amount of a combination of a 5-$HT_{2C}$ receptor agonist and a 5-$HT_6$ receptor antagonist, or a 8 salt, enantiomer or prodrug form of the said agonist and/or antagonist, and optionally a pharmaceutically acceptable carrier.

2. The pharmaceutical composition according to claim 1, wherein the 5-$HT_{2C}$ receptor agonist has a selectivity for the 5-$HT_{2C}$ receptor of at least about 10, relative to the 5-$HT_{2A}$ receptor, the 5-$HT_{2B}$ receptor, and the 5-$HT_6$ receptor, respectively.

3. The pharmaceutical composition according to claim 1 or 2, wherein the 5-$HT_6$ receptor antagonist has a selectivity for the 5-$HT_6$ receptor of at least about 10, relative to the 5-$HT_{2A}$ receptor, the 5-$HT_{2B}$ receptor and the 5-$HT_{2C}$ receptor, respectively.

4. The pharmaceutical composition according to claim 1, wherein the 5-$HT_{2C}$ receptor agonist is an arylpiperazine compound, such as a piperazinylpyrazine compound.

5. The pharmaceutical composition according to claim 1, wherein the 5-$HT_6$ receptor antagonist is selected from azepinoindoles, such as arylsulfone-substituted hexahydroazepinoindoles, and arylsulfonylindoles.

6. A process for preparing a pharmaceutical composition according to claim 1, wherein a 5-$HT_{2C}$ receptor agonist and a 5-$HT_6$ receptor antagonist in a combined therapeutic amount are intimately mixed with a pharmaceutically acceptable carrier.

7. A kit comprising a 5-$HT_{2C}$ receptor agonist and a 5-$HT_6$ receptor antagonist as a combined preparation for simultaneous, separate or sequential use in therapy of a disease related to the 5-$HT_{2C}$ receptor and the 5-$HT_6$ receptor.

8. The product according to claim 7, wherein the disease is selected from eating disorders, CNS disorders, urinary incontinence and glaucoma.

9. The product according to claim 8, wherein the disease is over-weight or obesity.

10. A method of treating a disease related to the 5-$HT_{2C}$ receptor and the 5-$HT_6$ receptor, comprising administering to a human or animal subject in need thereof a 5-$HT_{2C}$ receptor agonist and a 5-$HT_6$ receptor antagonist in sufficient amounts to provide a therapeutic effect.

11. The method according to claim 10, wherein the disease is selected from eating disorders, CNS disorders, urinary incontinence and glaucoma.

12. The method according to claim 11, wherein the disease is over-weight or obesity.

13. The method according to claim 10, 11 or 12, wherein the 5-HT$_{2C}$ receptor agonist and the 5-HT$_6$ receptor antagonist are administered as a combined pharmaceutical composition.

14. The pharmaceutical composition according to claim 2, wherein the 5-HT2$_C$ receptor agonist is an arylpiperazine compound, such as a piperazinylpyrazine compound.

15. The pharmaceutical composition according to claim 3, wherein the 5-HT$_6$ receptor antagonist is selected from azepinoindoles, such as a arylsulfone-substituted hexahydroazepinoindoles, and arylsulfonylindoles.

16. The pharmaceutical composition according to claim 1, wherein the 5-HT$_{2C}$ receptor agonist has a selectivity for the 5-HT$_{2C}$ receptor of at least about 20 relative to the 5-HT$_{2A}$ receptor, the 5-HT$_{2B}$ receptor, and the 5-HT$_6$ receptor, respectively.

17. The pharmaceutical composition according to claim 1 or 2, wherein the 5-HT$_6$ receptor antagonist has a selectivity for the 5-HT$_6$ receptor of at least about 20 relative to the 5-HT$_{2A}$ receptor, the 5-HT$_{2B}$ receptor and the 5-HT$_{2C}$ receptor, respectively.

18. The pharmaceutical composition according to claim 16, wherein the 5-HT2$_C$ receptor agonist is an arylpiperazine compound, such as a piperazinylpyrazine compound.

19. The pharmaceutical composition according to claim 17, wherein the 5-HT$_6$ receptor antagonist is selected from azepinoindoles, such as arylsulfone-substituted hexahydroazepinoindoles, and arylsulfonylindoles.

* * * * *

UNITED STATES PATENT AND TRADEMARK OFFICE
CERTIFICATE OF CORRECTION

PATENT NO.    : 6,818,639 B2
DATED         : November 16, 2004
INVENTOR(S)   : Björn M. Nilsson et al.

It is certified that error appears in the above-identified patent and that said Letters Patent is hereby corrected as shown below:

Column 10,
Line 23, after "a" and before "salt" delete "8".

Column 11,
Line 10, after "as" delete "a".

Signed and Sealed this

Twenty-fifth Day of October, 2005

JON W. DUDAS
*Director of the United States Patent and Trademark Office*